United States Patent [19]
Olsen

[11] Patent Number: 5,741,240
[45] Date of Patent: Apr. 21, 1998

[54] FLOAT TUBE URINAL

[76] Inventor: Mark B. Olsen, 7415 S. 700 East, Midvale, Utah 84047

[21] Appl. No.: 732,905

[22] Filed: Oct. 17, 1996

[51] Int. Cl.$^6$ .................................................. A61F 5/44
[52] U.S. Cl. ........................... 604/353; 604/327; 604/349
[58] Field of Search .................................. 604/323, 327, 604/329, 331, 349–353

[56] References Cited

U.S. PATENT DOCUMENTS

| | | |
|---|---|---|
| 940,077 | 11/1909 | Sherman . |
| 2,476,375 | 7/1949 | Kent .................................. 604/353 |
| 3,721,243 | 3/1973 | Hesterman et al. ................ 604/353 |
| 3,739,783 | 6/1973 | Broerman .......................... 604/349 |
| 4,020,843 | 5/1977 | Kanall . |
| 4,713,066 | 12/1987 | Komis . |
| 4,713,067 | 12/1987 | Rothenberg et al. . |
| 4,820,291 | 4/1989 | Terauchi et al. . |
| 4,846,816 | 7/1989 | Manfredi . |
| 4,901,375 | 2/1990 | Dahlgren . |
| 5,235,705 | 8/1993 | Belisle . |
| 5,267,989 | 12/1993 | Moyet-Ortiz . |
| 5,300,052 | 4/1994 | Kubo . |
| 5,375,265 | 12/1994 | Selzer . |

*Primary Examiner*—Robert A. Clarke
*Attorney, Agent, or Firm*—Thorpe, North & Western

[57] ABSTRACT

A float tube urinal of the present invention includes a urine inflow mechanism which is typically formed by a condom catheter formed of a condom (or other urinal) with an elongate tube extending therefrom. The condom catheter is connected to a housing with substantially rigid side walls, or sidewalls which, though flexible, are held apart by substantially rigid support structures, to prevent a compressive force from compacting a containment volume defined by the housing. A vent tube is attached to the housing to vent air in the housing as urine is received from the condom catheter.

18 Claims, 4 Drawing Sheets

FLOAT TUBE URINAL

BACKGROUND OF THE INVENTION

1. Field of the Invention

The present invention relates to a float tube urinal, and, more particularly, to a urinal which may be used with waders and the like when fishing or engaged in other similar activities in which it is difficult for the user to relieve himself without embarrassment and without compromising the environment.

2. State of the Art

The use of float tubes for those involved in fly fishing, other types of fishing and related activities has reached a high level of popularity. A float tube is typically an inflatable circular tube about 3 to 4 feet in diameter. A shell is formed for holding the tube, and has a seat formed therein so as to be positioned in the hole in the center of the tube. The person using a float tube typically wears waders which extend up to the chest to protect his legs and lower torso from prolonged exposure to the cold water.

Typically, the fisherman sits in the seat formed in the tube so that the buoyant tube holds the user's upper torso, arms and head above the water. Fins may be worn on the user's feet, to assist in movement of the float tube to a different location by kicking the legs. Because the arms are not needed to move or steer the float tube, the user can fish or prepare his fishing materials while casually propelling the float tube to a desired location.

One problem which develops in the use of float tubes is the difficulty for the user to urinate conveniently. When a fisherman needs to relieve himself, it is first necessary for him to move his tube over to the shore, a process which can take a considerable amount of time on a large lake. The fisherman must then remove his fins and get out of the float tube. He must then find appropriate privacy to complete the task. Such an arrangement creates three problems. First, the fisherman is distracted from fishing for a significantly long period of time. This is not only inconvenient, but can be very uncomfortable if procrastinated to the last minute.

Second, there is a significant environmental impact where large numbers of fisherman urinate along the shores of a lake or reservoir. The untreated human waste can affect other forms of life, as well as create biological risk. Additionally, in many locations the reservoir or lake may be the primary source of drinking water. Therefore, there is a significant risk of human waste entering a culinary water system.

A third, less serious concern, is the embarrassment that a person may feel as he paddles his float tube to the shore, knowing that other persons in the area know of his probable intent to relieve himself on the shore. This can result in cat calls and other embarrassing remarks from friends, in addition to the potential loss of a good fishing area, as other fisherman move into a hot area in his absence. Despite these long standing problems, this common practice continues in view of preferable alternatives.

It is well known that portable urinal devices exist, and have found general use in hospitals and other medical applications. There are numerous types of mechanisms which allow persons who are bed ridden to relieve themselves without need for an attending nurse. One common device for men is referred to as a condom catheter. The catheter has a condom shaped receptacle for fitting over the penis. A hollow tube typically extends from the container to channel the urine into a disposable receptacle.

While such mechanisms are well known in the medical art, they generally have been found to be unworkable in sport applications, such as with float tubes. Because urination involves gravity flow of fluid, urine receptacle must be placed below the level of the waist. In float tube applications in the water, however, the bag which receives the urine is disposed below the water surface. This water applies pressure resulting in a compressive force to the urine disposal bag, limiting the flow of urine into the receptacle, and occasionally forcing it back towards the user. This may be especially true if the bag is disposed on the front or rear of the leg, wherein it is exposed to additional pressure as the user kicks to move the float tube.

In addition, if the device does not include a venting mechanism, the combination of water pressure and air pressure in the bag (if the bag is not initially deflated) or around the bag (within the waders) can be a serious problem. As the user urinates, the air around the bag remains, placing pressure on the urine in the bag. Because the bag is disposed in the waders, there is generally little room for the bag to expand before the resilient waders or air trapped therein begin to provide a compressive force. Those who have attempted to use conventional urinals with float tubes have reported that the pressure build up can cause a considerable amount of pain if the person attempts to urinate more than a small quantity.

Thus, there is a need for a float tube urinal which is not hampered by water pressure and which has adequate mechanisms to compensate for the air pressure in or around the urine receptacle. Such a urinal should be private, easy to use and should enable the user to properly dispose of the urine in the receptacle.

SUMMARY OF THE INVENTION

It is an object of the present invention to provide a urinal system which may be used under restrictive clothing and other situations in which the urinal system may be under positive external pressure.

It is another object of the present invention to provide such a system which may be conveniently worn without restricting movement of the user.

It is another object of the present invention to provide such a system which enables a urine receptacle to expand without noticeable back pressure as urine is received, even when external pressures are present on the housing.

it is yet another object of the present invention to provide such a system which can be used by fisherman and the like to urinate without removing waders and without contaminating water sources with untreated human waste.

In is still another object of the present invention to provide such a system which enables the urine to be disposed of conveniently.

The above and other objects of the present invention not expressly enumerated are achieved through a float tube urinal which includes a urine inflow mechanism which is typically formed by a condom catheter or other urine receptacle (e.g. urine cup for females) which is connected by an elongate flexible tube to a urine receiving mechanism. The receptacle contains a mechanisms which prevents the receptacle from being collapsed by the water pressure which tests to collapse the waders.

In accordance with one embodiment, the urine receiving mechanism includes a substantially rigid housing. A vent mechanism, typically, an elongate flexible tube, may extend upwardly from the housing so as to enable the venting of air contained within or around the housing. Urine released into the condom catheter, or other urinal, flows by gravity through the flexible inflow tube and into the substantially rigid housing. Air within or around the housing (depending on the embodiment) is displaced from the housing and is forced through the vent mechanism to avoid pressure build-up.

In accordance with another aspect of the present invention, a rigid housing has a flexible receptacle disposed therein in a collapsed state. As urine flows into the housing, it is channeled into the receptacle, causing the receptacle to expand. Air which is contained within the rigid housing, but outside of the receptacle, is forced out of the housing and through the vent mechanism as the receptacle expands. Thus, the system prevents any pressure build-up, while obviating the risk that the urine will flow out of the vent mechanism and onto the user or into water supplies. In the alternative, the receptacle could be filled with air prior to use and the vent connected directly to the receptacle.

In accordance with another aspect of the present invention, the vent mechanism is disposed in fluid communication with the portion of the housing which holds the urine so as to enable urine to flow upwardly into the vent mechanism if the housing becomes full, thereby increasing the amount of urine which may be held within the system. The vent mechanism may include several wrappings of elongate tube so as to increase the holding capacity of the overall system. Additionally, a cap may be provided to prevent spilling of the urine out the vent mechanism while the user removes the waders.

In accordance with another aspect of the present invention, a plurality of check valves are disposed along the system to allow the urine to flow into the housing, but to prevent the urine from flowing back to the user, or out of the vent mechanism.

In accordance with another aspect of the present invention, the housing which is used to hold the urine is formed so as to substantially circumscribe the user's leg. The housing may be made of two separate rigid pieces of material, such as plastic, which form a shell for holding a flexible urine receptacle inside. The two pieces are joined together so as to fit around the user's leg while protecting the flexible receptacle from compressive forces, such as water pressure. In the alternative, the housing may be formed of a single piece of material which is sufficiently rigid that it withstands the compressive force of the water pressure, e.g. to a depth of up to six feet, but sufficiently flexible that two ends of the housing may be separated enough to enable the user to slide the housing onto and off of the leg when desired.

In accordance with yet another aspect of the present invention, a flexible receptacle may be used with a plurality of semirigid or rigid supports disposed therein to prevent the receptacle from being collapsed by the water pressure, while maintaining flexibility in the receptacle for adjusting to movements of the user's leg.

In accordance with still yet another aspect of the invention, a plurality of attachment mechanisms may be used to secure the housing to the user's leg so that the housing remains securely attached thereto.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
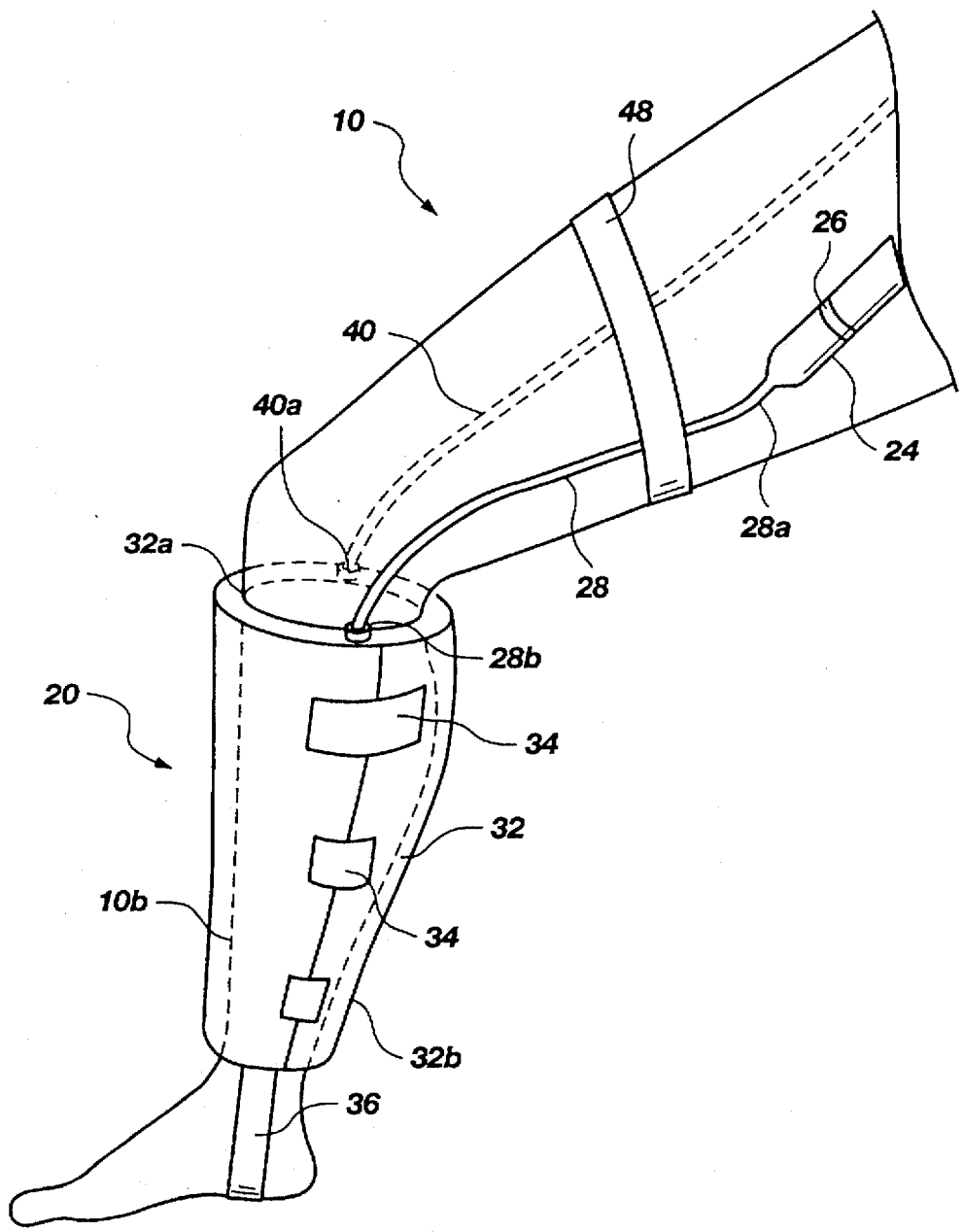
FIG. 1 shows a perspective view of a human leg with a urinal system made in accordance with the principles of the present invention attached thereto.

Referring to FIG. 1, there is shown a perspective view of a human leg, generally indicated at 10, having a urine disposal system, generally indicated at 20, attached thereto. The disposal system includes a catheter receptacle means for connection to the user. As shown in FIG. 1, the catheter connection means is in the form of a condom catheter. The condom catheter includes a condom 24. Those familiar with urine catheters will recognize that numerous types of condom catheters are available. A small adjustable elastic band 26 may be used to ensure that the condom 24 is properly held on the penis.

Attached to a distal end of the condom 24 is a urine inflow tube 28. A first end 28a of the urine inflow tube connects to the condom 24. Typically, the two are formed integrally with one another. However, other, removable attachments can also be used.

The opposing, second or distal end 28b of the urine inflow tube 28 connects with a receptacle formed by a housing 32 which is disposed about the lower portion 10b of the leg—typically along the calf. As shown in FIG. 1, the housing 32 can be formed of two pieces, with a plurality of attachments 34 attached thereto for holding the pieces of the housing together. Typically, the attachments will be made of hook and loop fastener due to the durability of the material, as well as its resistance to damage by water.

In the alternative, the housing 32 can be made of a single piece of material, and the attachments 34 are merely used to hold opposing ends together. The housing will typically be made of a substantially rigid material. By substantially rigid, it is not meant that the housing cannot bend. Rather, as used herein, substantially rigid means that the material is sufficiently firm to transmit nominal compressive force to the containment volume in the interior of the housing up to a depth of at least 6 feet of water. Thus, when the housing 32 is formed of a single piece of material, the walls of the housing will typically have enough resiliency to enable the housing to temporarily deform while being removed from the user's leg. Those skilled in the art will appreciate that there are numerous plastics which have an appropriate balance of rigidity and flexibility.

As shown in FIG. 1, the housing 32 can be contoured to the general shape of a user's leg to hold the housing in place as the user moves his legs. The housing 32 has a concave inner wall 32a which is configured for wrapping about the leg 10, and a convex outer wall 32b which forms an arch-shaped support which is disposable against the waders. To further secure the positioning of the housing 32, an ankle or foot strap 36 may be used. Keeping the housing 32 in place is important because kicking the legs is the primary means of locomotion with float tubes and other similar watercraft.

Disposed on the opposite side of the leg 10 and represented in dashed lines is an outflow or vent tube 40. A proximal end of the vent tube 40 is attached to the housing 32, while the opposing distal end (FIG. 5) extends upwardly beyond the top of the waders. The vent tube 40 allows air contained within the housing to be vented to the atmosphere. If the air is not vented, air pressure can inhibit the flow of urine and occasionally cause backflow which results in the soiling of the user's clothing. By venting the air in the containment volume of the housing 32 as urine is received from the condom catheter 24, there is no creation of back pressure.

As will be explained with more detail below, the vent tube 40 can be used in two configurations. In one, a receptacle placed in the housing is not in direct fluid communication with the vent tube. As urine flows into the receptacle it expands, forcing air in the housing out the vent tube 40. In such a configuration, the urine cannot flow out of the vent tube 40, and remains in the receptacle for easy disposal.

In the alternative, the vent tube 40 can be disposed in communication with the housing or other type of receptacle disposed therein for receiving the urine. In the event that the housing 32 overfills, the excess urine can flow up the vent tube 40. In such a configuration, the vent tube 40 is used to expand the total volume of the system 20 available for urine collection. Generally the force with which the user urinates will not be sufficient to raise urine out of the upper end of the vent tube 40, thereby preventing contamination of water sources with human waste.

Both the urine inflow tube 28 of the condom catheter and the vent tube 40 can be held in place along the user's leg by an elastic or otherwise adjustable strap 48. The strap 48 keeps the tubes 28 and 40 from rubbing against the user's leg in such a manner to irritate the skin, and preventing the urine inflow tube from being pulled from the housing 32 or that the condom 24 is pulled off the user's penis.

Figure 2:
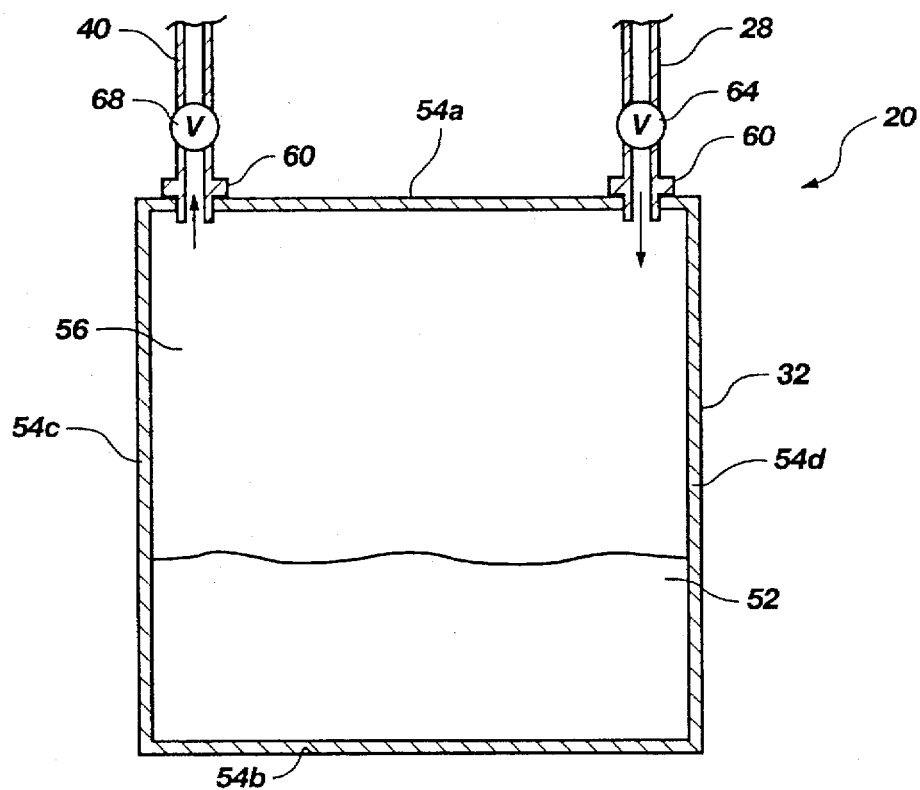
FIG. 2 shows a cross-sectional view of a housing and tubing made in accordance with the principles of the present invention.

Referring now to FIG. 2, there is shown a cross-sectional view of a receptacle in the form of a housing 32 made in accordance with the principles of the present invention, along with fragmented views of the urine inflow tube 28 and the vent tube 40. The urine inflow tube 28 and the vent tube 40 are each attached to the housing 32 by snap in connectors which enable the tubes to be easily removed from the housing for cleaning.

As urine flows out of the urine inflow tube 28 and into the housing 32, the air in the housing is forced up the vent tube 40. If sufficient quantities of urine 52 are present in the containment volume 56, the urine also may travel up the vent tube 40, thereby enabling the system to hold a larger amount of urine.

If the housing 32 were made of sheets of plastic, as are most receptacles in urinals used for immobile persons, the water pressure would severely restrict the flow of urine 52 into the housing, and urine in the housing would be more likely to be forced from the housing, potentially spilling on the user or into water supplies. By making a housing 32 which is substantially rigid, i.e. the top and bottom walls 54 a and 54 b and the inner and outer side walls 54 c and 54 d are sufficiently rigid to have nominal bending at 1.2 atmospheres (approximately 6 feet of water), the housing 32 forms a receptacle with internal support mechanism which are rigid enough to prevent such situations. Thus, the urinal system 20 may be used without discomfort to the user.

Also shown in FIG. 2, are snap-in connectors 60 which may be used to detach either the urine inflow tube 60 for draining the housing 32, and for cleaning. Such connectors should hold sufficiently and prevent accidental removal while in use.

A plurality of valves 64 and 68 may be disposed in the urine inflow tube 28 and the vent tube 40. The valve in the urine inflow tube will typically be a one-way valve to prevent backflow onto the user. If a valve is disposed in the vent tube 40, it will typically be a float type valve which allows air to pass while preventing the flow of liquid out of the vent tube.

Figure 3:
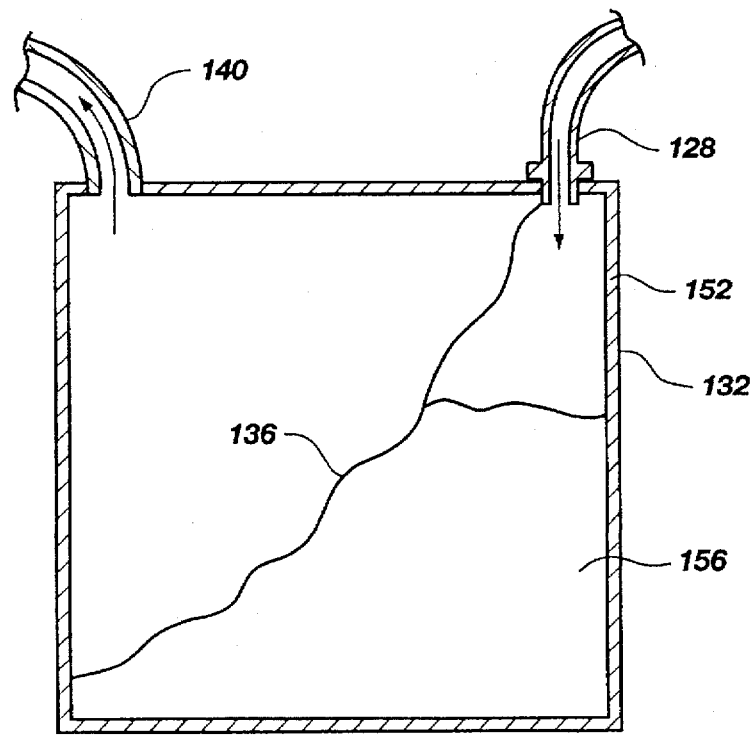
FIG. 3 shows a cross-sectional view of another embodiment of a housing and a urine receptacle made in accordance with the principles of the present invention.

Referring now to FIG. 3, their is shown an alternate embodiment of the receptacle in the form of a housing, 132, along with the urine inflow tube 128 and the vent tube 140. Disposed inside of the housing 132 is a urine receiving sack 136 which is disposed in fluid communication with the urine inflow tube 128 so as to receive urine 156 from the urine inflow tube. Typically, the receiving sack 136 is placed in the housing 132 in a collapsed state. As urine 156 is received from the urine inflow tube 128, the receiving sack 136 fills and expands.

As the receiving sack 136 expands due to the urine, the air contained in the housing 132 is vented through the vent tube 140. In such a manner, the air which passes out of the vent tube 140 never comes into direct contact with the urine 156, thereby preventing the venting of foul smelling air, and also preventing the urine from accidentally being forced out of the vent tube. The corresponding disadvantage is that the housing 132 must be larger to accommodate the same amount of urine 156 as the embodiment shown in FIG. 2 can accommodate due to the volume of urine which may be disposed in the vent tube 40. Of course, the need for venting depends, in part, on the volume of the receptacle.

In the alternative to having a collapsed sack with air about it in the housing, the bag could be filled with air so that little if any air is disposed between the housing and the sack. In such a situation, the vent would be connected directly to the sack.

Once the user is finished fishing, the receiving sack 136 may be removed through a wall 152 configured as a door. In the alternative, the urine may be drained out the urine inflow tube 128.

Those skilled in the art will appreciate that the housing 32 or 132 need not be a continuous walled structure. Rather, the housing 32 or 132 must only be a support structure sufficiently resistant to compressive force and that the flow of urine into the housing is not impeded. Thus, for example, the housing could be formed from mesh or plastic grids which reduce weight.

Figure 4:
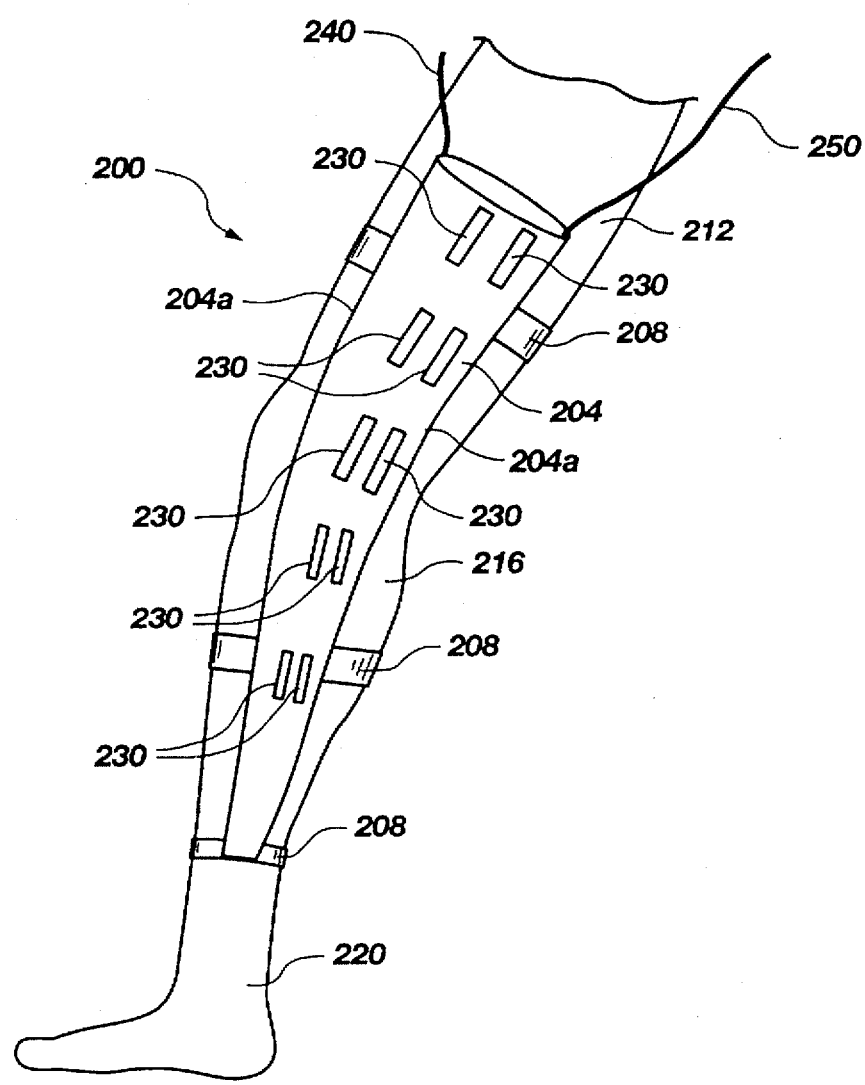
FIG. 4 shows a perspective view of still another embodiment of the present invention disposed on a human leg.

In the alternative, a support mechanism could be built into or placed in the receptacle as is shown in FIG. 4. The receptacle 200 includes opposing flexible walls configured to form a flexible sack 204. The flexible sack 204 is sufficiently long to extend along the user's leg. A plurality of support straps 208 connect to the lateral sides 204 a of the flexible sack 204 and enable the sack to be comfortably held to the user's leg 212.

The length of the sack 204 will depend on the desired volume, as well as the orientation which is preferred by the user. For example, rather than extending along the user's leg 212, the flexible sack 204 could be wrapped about the user's calf 216 or ankle 220 if desired. In such a configuration, the sack would typically be wider and shorter than the sack 204 shown in FIG. 4.

To prevent water pressure from collapsing the opposing walls of sack 204 together, a plurality of support structures 230 are disposed within the sack. The support structures 230 may be made from a variety of rigid or semi-rigid materials. The only condition is that the structures be sufficiently large to maintain a containment volume within the sack 204, and sufficiently rigid to inhibit collapse of the sack 204 due to water pressure when the fisherman is in the float tube. Thus, for example, small segments of foam one inch high, one inch wide and three inches long could be glued to the opposing walls of the sack 204 to maintain a minimum available volume within the sack. The foam segments will typically be resilient enough to resist the compressive forces of the water pressure, and yet have sufficient give that they can conform slightly to distortions of the sack 204 caused by bending the leg 212 or bumping into rocks and the like.

Those skilled in the art will appreciate that numerous alternatives exist to the foam structures. One example of alternative support structures includes inflatable pockets within the sack 204 to prevent the opposing walls of the sack from collapsing. In light of the present application, those skilled in the art will appreciate numerous other support structures that will work equally well. The only critical limitation is that at least a portion of the sack is held open sufficiently to hold a desired amount of urine.

As is shown in FIG. 4, the support structures 230 preferably are spaced to enable free flow of liquid between the sides of the sack 204. In the event that the sack 204 is forcefully impacted by a rock, tree branch, etc., the flowability of fluid helps prevent rupture. The spacing of the support structures 230 also facilitates bending of the user's leg 212 without placing excessive pressure on the support structures or the urine contained within the sack 204.

While shown in FIG. 4 as being disposed in two lines, the support structures 230 can be disposed in any desired configuration. Thus, several rows of support structures 230 may be provided, or the support structures may be placed in various patterns to minimize the portion of the sack 204 which is compressible. While the position of the support structures 230 shown in FIG. 4 would allow the water pressure to collapse the areas of the sack 204 adjacent the lateral sides 204 a, the support structures are positioned to provide a containment space capable of holding the desired amount of urine. Those skilled in the art will be able to construct such sacks to maximize volume while minimizing the size of the sack and support structures contained therein.

In use, urine flows in through the urine inflow tube 250 and into the sack 204. In one alternative, the vent tube 240 is attached to the sack 204. As the sack 204 fills, the air contained within the sack is forced into the vent tube 240. Those skilled in the art will appreciate that if the sack 204 is sufficiently large, 240 vent tube need not be attached to the sack provided because the compression of the air caused by urine inflow will result in a minimal increase in back pressure. Rather, a vent tube, such as vent tube 240 will simply be provided to vent air around the sack 204 within the waders, to allow the sack to fill properly.

Figure 5:
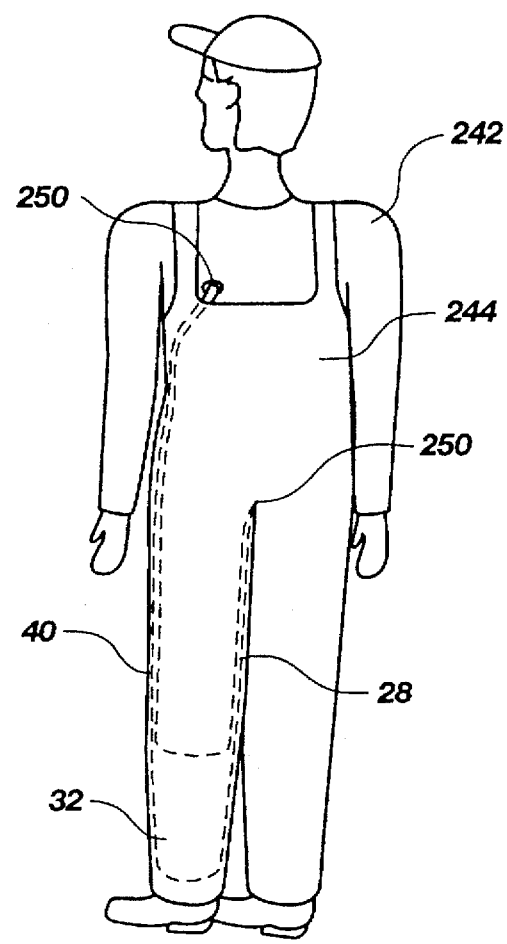
FIG. 5 shows a rear view of a person wearing waders having a urine disposal system made in accordance with the principles of the present invention disposed therein.

Referring now to FIG. 5, there is shown a fisherman 242 wearing a pair of waders 244 as are typically used with float tubes and the like. The waders extend up to the fisherman's chest slightly below the armpit. Those familiar with wearing such waders will appreciate that urinating is a significant problem. This problem is resolved, however, by the urine disposal system of the present invention. Instead of traveling to shore and finding a tree or other structure behind which to hide while urinating, the user need only release the urine into the condom catheter, of which only the urine inflow tube 28 is shown. The urine inflow tube 28 will typically be made from a semi-rigid material, such as polyvinylchloride approximately ⅜ths to ½ inch in diameter. Whatever material is used, it must be sufficiently firm to prevent accidental collapse by pressure from the waders or by accidental movement from the user.

From the urine inflow tube 28, the urine passes into the urine containment area of the housing 32, the air which is displaced is forced up the vent tube 40, thereby preventing the air from being compressed and forming a back pressure which might be uncomfortable or even painful to the user. A cap 250 may be placed on the vent tube 40 to prevent spillage when the user removes the waders. Additionally, the cap can be left in place, except during urination, to prevent odors from escaping from the urine containment area.

If the configuration of FIG. 2 is used, the capacity of the vent tube 40 to hold additional quantities of urine can be improved by providing a vent tube with a helical coiling along at least the lower portion thereof. The coiling maximizes the volume of the vent tube 40 which may be used for holding urine, while lowering the risk that the urine will flow out of the distal end of the vent tube.

As is clearly shown in FIG. 5, it is important the housing 32 is disposed below the crotch 250 of the waders 244. If the housing 32 is disposed above the crotch 250 of the waders, the user must force the urine upwardly into the housing. This creates a significant risk that back pressure will develop. Additionally, any urine not passing a one-way flow valve or other flow control device will leak back to the user. Such a situation would be uncomfortable for most users, and will often leave the user's clothing soiled.

Thus there is disclosed an improved float tube urinal and a method of use. Those skilled in the art will appreciate that numerous modifications may be made without departing from the scope and spirit of the present invention. The appended claims are intended to cover such modifications.

What is claimed is:

1. A containment device for receiving and containing urine and being capable of direct attachment and support along a leg of an individual between the leg and external forces that would tend to collapse the containment device against the leg, the containment device being configured for use by a person using a float tube, said device comprising:

a substantially rigid case having opposing inner and outer walls, said inner wall being configured for support against the leg of the individual, said outer wall being configured for counter support against the external forces, said rigid case defining a containment volume between the inner and outer walls for receiving and temporarily containing the urine;

support means extending between the inner and outer walls for maintaining the containment volume and resisting collapse of the outer wall against the inner wall in response to the external forces;

a fluid containment compartment positioned within the containment volume;

inlet means for transporting urine from the individual to the containment compartment; and vent means disposed in communication with the containment volume between the inner and outer walls for venting air from the containment volume to thereby facilitate receiving and temporarily containment of urine within the containment volume, the vent means comprising a flexible tube configured for extending from the case to a position out of a pair of waders to vent air from the containment area.

2. A device as defined in claim 1, wherein the rigid case includes a bottom wall attached to a lower end of the inner and outer walls and including means for supporting any fluid contained in the containment volume.

3. A device as defined in claim 1, wherein the inner wall is configured with a concave interior surface having a curvature corresponding the curvature of the leg against which the interior surface is supported, said outer wall having a convex exterior surface which supplies an arch support against the exterior forces.

4. A device as defined in claim 1, wherein the rigid case includes fluid containment means within the containment volume, said rigid case having an opening at an upper end for receiving urine from the inlet means.

5. A device as defined in claim 4, wherein the fluid containment means comprises interior wall structure of the rigid case which is configured as a fluid tight container.

6. A device as defined in claim 4, wherein the fluid containment means comprises a urine receiving sack which is removably insertable within the containment volume, said urine receiving sack including an opening for attachment at the inlet means and means for attachment to the vent means so as to vacate air from within the urine receiving sack when urine is received in the urine receiving sack.

7. A device as defined in claim 1, wherein a sack is disposed in the containment volume in the rigid case for receiving urine, and wherein the vent means is disposed in communication with the rigid case to permit displacement of air from the containment volume in response to inflow of urine, the sack being disposed so as to isolate the urine from the air contained in the containment volume and vented through the vent means.

8. A device as defined in claim 1, wherein the device further comprises valve means disposed in the vent means for preventing urine to flow out through the vent means.

9. A device as defined in claim 1, wherein the device further comprises one-way valve means disposed in the inlet means to prevent urine from flowing from the case to the user.

10. A urine disposal system for use with a pair of waders, the system comprising:

a housing defining a containment volume and having a plurality of substantially rigid side walls disposed at opposing sides of the containment volume and configured to prevent compressive force to the side walls from collapsing the containment volume, the housing having a first side configured for placement adjacent a human leg;

urine inflow means for directing urine into the housing; and vent means connected to the housing for venting air contained in the housing when urine flows into the housing, wherein the vent means comprises an elongate flexible tube attached to the housing, the tube being of sufficient length to extend from the housing to the tog of a pair of waders when the housing is disposed in the waders below the crotch thereof.

11. The system of claim 10, wherein the system further comprises a urine containment sack disposed within the housing for receiving urine from the urine inflow means.

12. The system of claim 11, wherein the vent means is disposed out of fluid communication with the urine receiving sack such that urine within the urine containment sack is prevented from flowing into the vent means by the urine containment sack.

13. The system of claim 11, wherein the urine containment sack is removable from the housing.

14. The system of claim 10, wherein the fluid inflow means comprises a condom catheter.

15. The system of claim 10, wherein at least a portion of the housing is arcuate.

16. The system of claim 10, wherein the device further comprises valve means disposed in the vent means for preventing urine to flow out through the vent means.

17. A method of making a float tube urinal, the method comprising:

a) selecting a compression resistant housing;

b) attaching a urine inflow tube from the user to the housing for channeling urine from a user to the housing; and c) attaching a flexible vent tube to the housing so as to vent air in the housing when urine is received from the urine inflow tube, the flexible vent tube being sufficiently long to extend out of a pair of waders worn by a user, when the housing it attached to the user's leg.

18. A method for using a float tube urinal by a person wearing waders, and the method comprising:

a) selecting a housing having an inner containment volume and being configured to resist compressive forces, said housing and inner containment volume having a urine inflow tube and a flexible vent tube;

b) attaching the urine inflow tube to the person such that urine excreted by the person flows down the urine inflow tube and into the housing; and c) positioning the flexible vent tube so that an end of the vent tube extends beyond the waders such that flow of urine into the housing forces air out of the housing and out of the opposing end of the event tube.

* * * * *